United States Patent [19]

Inglis et al.

[11] Patent Number: 5,386,826
[45] Date of Patent: Feb. 7, 1995

[54] TRACHEAL TUBE ASSEMBLIES

[75] Inventors: Timothy J. J. Inglis, Leeds; Michael R. Millar, Wincester, both of Great Britain

[73] Assignees: Smiths Industries Public Limited Company; University of Leeds Industrial Services Limited, London, England

[21] Appl. No.: 781,138

[22] PCT Filed: Feb. 15, 1991

[86] PCT No.: PCT/GB91/00234
§ 371 Date: Apr. 29, 1992
§ 102(e) Date: Apr. 29, 1992

[87] PCT Pub. No.: WO91/12844
PCT Pub. Date: Sep. 5, 1991

[30] Foreign Application Priority Data

Feb. 21, 1990 [GB] United Kingdom ............... 9003857
Feb. 21, 1990 [GB] United Kingdom ............... 9003859

[51] Int. Cl.⁶ .......................................... A61M 16/00
[52] U.S. Cl. ......................... 128/207.14; 128/200.23; 604/282

[58] Field of Search ............... 128/207.14, 207.17, 128/658, 911, 912, 200.23; 604/96, 158, 164, 171, 172, 265, 239, 282

[56] References Cited

U.S. PATENT DOCUMENTS

| | | | |
|---|---|---|---|
| 2,765,792 | 10/1956 | Nichols | 128/200.26 |
| 3,039,469 | 6/1962 | Fountain | 128/200.26 |
| 3,169,529 | 2/1965 | Koenig | 128/207.14 |
| 3,225,767 | 12/1965 | Smith | 128/200.26 |
| 3,498,286 | 3/1970 | Polanyi | 604/282 X |
| 5,078,702 | 1/1992 | Pomeranz | 128/658 X |
| 5,119,811 | 6/1992 | Inglis | 128/207.14 |

*Primary Examiner*—Edgar S. Burr
*Assistant Examiner*—Eric P. Raciti
*Attorney, Agent, or Firm*—Pollock, Vande Sande & Priddy

[57] ABSTRACT

A tracheal tube assembly comprises an outer tube and an inner cannula that is insertable within and removable from the outer tube. The inner cannula has an inner surface of a flexible plastic material such as PVC to which respiratory secretions cling. The outer surface of the cannula is of a material having a lower friction than the inner surface and may be a helical filament or a continuous layer. The machine end of the inner cannula projects beyond the outer tube to form a flexible portion which is terminated with a coupling.

10 Claims, 1 Drawing Sheet

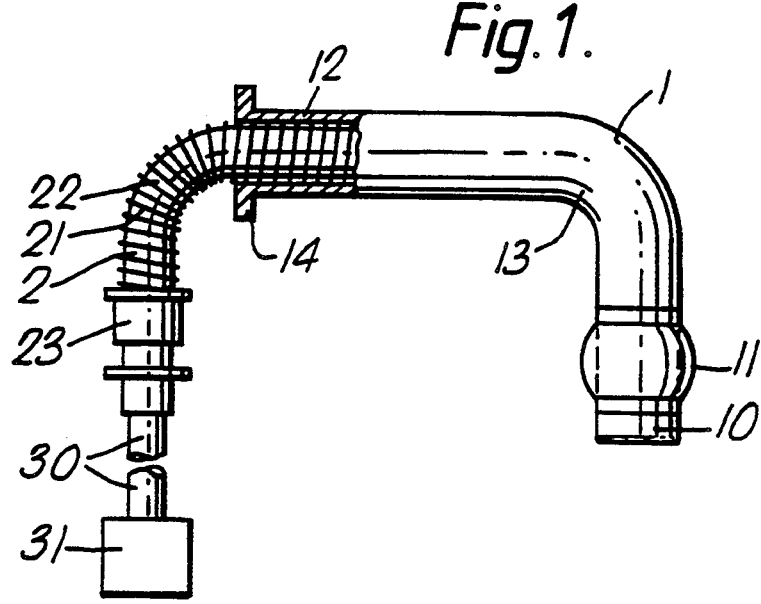
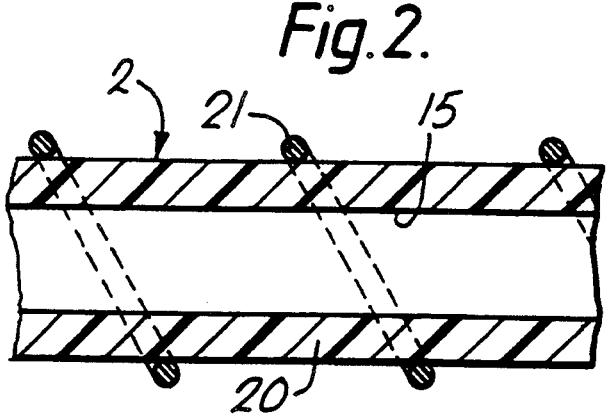
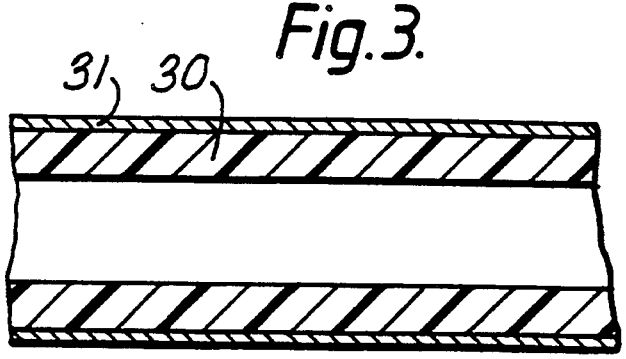

TRACHEAL TUBE ASSEMBLIES

BACKGROUND OF THE INVENTION

This invention relates to tracheal tube assemblies of the kind having an outer tube and an inner cannula that is insertable within and removable from the outer tube.

With such assemblies, the inner cannula is removed and replaced periodically when secretions have built up on the cannula to an extent that there is a risk of blockage. Tracheal tube assemblies are described, for example, in U.S. Pat. No. 3,948,274, GB 2056285B, GB 1099277, GB 125754, WO 90/04992, FR 2539998A, DE 72467, DE 1268313, EP 0107779A, U.S. Pat. Nos. 4,817,598, 3,659,612, 4,009,720, 3,088,466, 4,315,545, 2,765,792, 3,169,529, 3,263,684, 3,334,631, 3,587,589, 3,688,774, 3,731,692, 3,889,688, 3,948,273, 3,973,569, 3,987,798, 4,033,353, 4,045,058, 4,235,229, 4,471,776, 4,593,690.

In order to ensure as large as possible bore through the assembly, the wall of the inner cannula must be as thin as possible and the external diameter of the inner cannula must be as close as possible to the internal diameter of the outer tube. This, however, increases the risk of kinking of the cannula on insertion, especially where friction with the outer tube causes a greater axial force to be exerted on the cannula. A further problem arises because, if the cannula is made of a low-friction material, these tend not to enable respiratory secretions to cling to them readily, thereby increasing the risk that secretions will become dislodged and fall into the bronchi and lead to infection.

It is an object of the present invention to provide an improved inner cannula for a tracheal tube assembly.

SUMMARY OF THE INVENTION

According to one aspect of the present invention there is provided a tracheal tube assembly of the above-specified kind, characterized in that the inner cannula has an inner surface to which respiratory secretions will cling, and an outer surface of a different material with a lower coefficient of friction than the inner surface.

The outer surface may be a continuous layer of a filament extending around the outside of the cannula. The filament may extend helically around the tube and may be of a metal. Alternatively, the outer surface may be provided by a low friction plastics material. The inner surface is preferably smooth and may be of a flexible plastics material such as PVC. The machine end of the inner cannula may project beyond the machine end of the outer tube and provide a flexible portion, the inner cannula having a coupling on its machine end.

BRIEF DESCRIPTION OF THE DRAWINGS

A tracheal tube assembly including an inner cannula, in accordance with the present invention, will now be described, by way of example, with reference to the accompanying drawings, in which:

FIG. 1 is a partly sectional side elevation view of the assembly;

FIG. 2 is a cross-section to a larger scale of a part of the inner cannula; and

FIG. 3 is a cross-section of an alternative inner cannula.

DESCRIPTION OF THE PREFERRED EMBODIMENTS

With reference first to FIG. 1, the assembly comprises an outer tracheostomy tube 1 and an inner cannula 2.

The tracheostomy tube 1 is of conventional construction having a patient end 10 which, in use, is located in the patient's trachea and has an inflatable cuff 11 that seals the tube with the trachea. The machine end 12 of the tube 1 extends at approximately right angles to the patient end, there being an abrupt bend portion 13 between them. A flange 14 is located at the machine end 12 where it emerges from the tracheostomy at the surface of the patient's neck and to which it is secured by a tape (not shown).

With reference now also to FIG. 2, the inner cannula 2 comprises an inner flexible tube 20 of PVC which has a circular section and a smooth internal bore 15. Around the external surface of the tube 20 extends a filament in the form of a helical coil 21 of stainless steel wire. The coil 21 is secured to the external surface of the tube 20 and may be partly embedded in it, providing that the outer surface of the coil is exposed.

A filament of other low friction materials, such as a low-friction plastics could be used. The filament need not be wound in a helical coil but could extend around the inner tube by being a part of a braided sleeve.

The thickness and nature of the inner tube 20 is such that, by itself, it would be very prone to radial deformation and kinking. It also has a relatively high coefficient of friction which would make insertion in the outer tube 20 difficult, especially in view of the fact that the external diameter of the inner cannula should be as close as possible to the internal diameter of the tube 1. The coil 21, however, serves two purposes. Firstly, it gives the cannula 2 radial rigidity so that it is immune from kinking in normal use. Secondly, the wire coil 21 has a relatively low coefficient of friction so that it provides the exterior of the cannula with a surface that can slide readily along the inside of the outer tube 1. This enables the inner tube 20 to be made of a material such as PVC to which respiratory secretions will cling but which has a relatively high coefficient of friction. Various different factors determine the degree to which secretions will cling to the inner tube 20. For example, a highly polar material will improve adhesion as will the presence of microscopic surface formations. A hydrophilic material may also provide a better site for adhesion of the secretion. The flexible nature of the inner tube 20 and the coil 21 means that the inner cannula can have a high radial rigidity but be highly flexible, enabling it easily to be pushed through the outer tube 1 around the abrupt bend portion 13. It is also advantageous that the bore 15 of the inner cannula 2 be as smooth as possible so as to reduce turbulence of airflow along the tube. This has been found to reduce the risk of accumulated secretions being loosened by airflow along the tube.

The length of the inner cannula 2 is chosen to be longer than the outer tube 1 so that, when the patient end of the inner cannula is flush with the patient end of the outer tube 1, a portion 22 at the machine end of the cannula projects from the machine end of the outer tube. This portion 22 is flexible relative to the outer tube and is typically about 40-50 mm long. At its machine end, the cannula 2 has a coupling 23 by which the assembly is connected via tubing 30 to a ventilator 31.

The flexible nature of the portion 22 means that the tubing 30 can be led away from the tracheostomy in any direction. This avoids the need for using a separated angled coupling or flexible interconnection between the assembly and ventilation tubing 30. It also prevents undue stress being exerted on the tracheostomy.

The inner cannula 2 may have a stop (not shown) on its outer surface, which is located to be positioned at the flange 14 of the outer tube 1, when the patient end of the inner cannula is flush with the patient end of the outer tube. The stop may be arranged to seal with the flange, or in the machine end of the outer tube 1, to prevent passage of gas between the outside of the inner cannula and the inside of the outer tube.

It is not essential for the outer surface of the cannula to be provided by a filament. Instead, as shown in FIG. 3, the outer surface could be provided by a continuous layer 32 of a relatively low friction plastics material such as a polyolefin, for example, a low density polyethylene or polypropylene. The outer layer 32 may be coextruded with the inner layer 33 which may be of PVC. The tube of FIG. 3 will be more prone to kinking than that of FIG. 2 making it less suitable for providing a flexible coupling at the machine end of the outer tube.

It will be appreciated that the assembly could be an endotracheal tube assembly instead of a tracheostomy tube assembly.

We claim:

1. A tracheal tube assembly for use in ventilation of a patient, said assembly being sized for location in the trachea of a patient and comprising an outer tube and an inner cannula that is insertable within and removable from the outer tube, said inner cannula having an inner surface of a first material to which respiratory secretions will cling, and an outer surface of a second material that is different from said first material and provides said outer surface with a lower coefficient of friction than said inner surface to facilitate insertion of said inner cannula into, and removal of said inner cannula from, said outer tube.

2. A tracheal tube assembly according to claim 1 wherein said outer surface is a continuous layer of said second material.

3. A tracheal tube assembly according to claim 1, wherein said outer surface is provided by at least one filament extending around the outside of the cannula.

4. A tracheal tube assembly according to claim 3, wherein said filament extends helically around the tube.

5. A tracheal tube assembly according to claim 3 or 4, wherein said filament is of a metal.

6. A tracheal tube assembly according to any one of claims 1 to 4, wherein said outer surface is provided by a low friction plastics material.

7. A tracheal tube assembly according to any one of claims 1 to 4 wherein said inner surface is smooth.

8. A tracheal tube assembly according to any one of claims 1 to 4 wherein said inner surface (20, 30) is of a flexible plastics material.

9. A tracheal tube assembly according to claim 8, wherein said inner surface is PVC.

10. A tracheal tube assembly according to any one of claims 1 to 4 wherein the inner cannula has a machine end that projects beyond a machine end of the outer tube and provides a flexible portion, the inner cannula having a coupling on its machine end.

* * * * *